United States Patent [19]

Bertholet et al.

[11] Patent Number: 4,772,726
[45] Date of Patent: Sep. 20, 1988

[54] PREPARATION OF MELATONINE AND MEXAMINE

[75] Inventors: Raymond Bertholet, La Tour-de-Peilz; Pierre Hirsbrunner, Corseaux, both of Switzerland

[73] Assignee: Nestec S. A., Vevey, Switzerland

[21] Appl. No.: 924,107

[22] Filed: Oct. 31, 1986

Related U.S. Application Data

[60] Continuation of Ser. No. 680,766, Dec. 12, 1984, abandoned, which is a division of Ser. No. 510,167, Jul. 1, 1983, Pat. No. 4,506,080.

[51] Int. Cl.[4] .............................................. C07D 209/16
[52] U.S. Cl. .................................... 548/504; 548/507
[58] Field of Search ............................... 548/504, 507

[56] References Cited

U.S. PATENT DOCUMENTS

3,449,213  6/1969  Littell, et al. ...................... 548/504
3,686,213  8/1972  Poletto et al. ...................... 548/507

FOREIGN PATENT DOCUMENTS

2532308  12/1976  Fed. Rep. of Germany ...... 548/504

OTHER PUBLICATIONS

Flaugh, et al., "Synthesis and Evaluation of... Melatonin...," *J. Med. Chem.* 22, pp. 63–69 (1978).
Pollack and Bender, "Alkaline Hydrolysis of p Nitro-acetanilide...," *J. Am. Chem. Soc.*, 92:7190 (1970).
McOmie, J. F. W., *Protective Groups in Organic Chemistry*, Plenum Press, NY (1973), pp. 45–50.
Rogawski, et al., "Melatonin: Deacylation to 5-Methoxytryptamine...", Chem Abst. 91:137923(b) (1979).
A. Kiyoshi, et al., "DNA-DNA Hybridization at Low Temperature..., " *Chem. Abst.* 73:171(p) (1970).
Kanduc, Darja, "Methylation Patterns pf TRNA...", *Chem. Abst.* 92, 209815p (1979).
Barciszewski, et al., "Chemical Probes for TRNA Tertiay Structure...," Chem. Abst. 98:122373(t).
Christen, H. R., Fundamentals of Organic Chemistry (1970), pp. 1–4.

*Primary Examiner*—Mary E. Ceperley
*Attorney, Agent, or Firm*—Vogt & O'Donnell

[57] ABSTRACT

Melatonine is obtained by methylating N-acetyl serotonine in the 5-position. Mexamine is obtained by deacetylating melatonine in a hot alkaline solution containing a water-insoluble alcohol and acidifying the alcohol phase with hydrochloric acid.

21 Claims, No Drawings

PREPARATION OF MELATONINE AND MEXAMINE

This is a continuation of co-pending application Ser. No. 680,766, filed on Dec. 12, 1984, now abandoned, which in turn is a divisional of application Ser. No. 510,167, filed July 1-83, now U.S. Pat. No. 4,506,080.

BACKGROUND OF THE INVENTIONS

The present invention relates to a process for the separation of serotonine from coffee wax and also to processes for the preparation of certain derivatives of serotonine, more particularly N-acetyl serotonine, melatonine and mexamine.

Serotonine, the chemical name of which is 5-hydroxytryptamine, is an indolic alkaloid having the following formula:

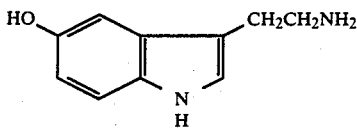    I

This alkaloid plays an important role in the metabolism of the brain and has vasoconstrictor, antihypertensive and antiallergenic properties, and may be used for the treatment of psychoses, migraine and for the control of excessive smoking.

The derivatives of serotonine also possess pharmacological properties as follows:

N-acetyl serotonine, the chemical name of which is N-acetyl-5-hydroxytryptamine has antihypertensive properties.

Melatonine the chemical name of which is N-acetyl-5-methoxytryptamine, is secreted by the pineal gland and possesses a regulatory activity on the circadian cycle. In addition, its use in an amount of 1-2 mg/day can induce ovulation in sheep, which is of considerable economic importance. Moreover, it has been shown that melatonine can induce sleep in man in an amount of 1-3 mg/kg body weight.

Mexamine, the chemical name of which is 5-methoxytryptamine hydrochloride, has been proposed as a sedative and as a radioprotective agent.

In French Pat. Nos. 2333793 and 2371429 there is described a process for the separation of serotonine from coffee wax in which a solution of coffee wax in an alcohol is subjected to an alkaline hydrolysis using a strong base in an inert atmosphere, after which the reaction medium containing the serotonine is recovered. In French Pat. No. 2333793 the alcohols used are those insoluble or partially soluble in water having from 4 to 8 carbon atoms e.g. isobutanol, pentanols or hexanols. However the yield obtained is relatively low (8.6 grams serotonine per kilogram of wax) because only about 50% hydrolysis takes place. In French Pat. No. 2371429 the alcohol used is benzyl alcohol or one of its homologues but the yield is not increased because the alcohol forms the corresponding primary amine which is difficult to separate from the serotonine and, in addition, a β-carboline is formed from serotonine which impairs the yield. We have now found, surprisingly, that by using certain glycols or glycol ethers as the solvent in a process similar to that described in the above-mentioned French Patents, a much more complete hydrolysis can be achieved without provoking the formation of amines and β-carboline and leading to a yield about 3.5 times greater.

SUMMARIES AND DETAILED DESCRIPTION OF THE INVENTIONS

Accordingly the present invention provides a process for the separation of serotonine from coffee wax wherein a solution of coffee wax is subjected to alkaline hydrolysis using a strong base in the presence of water in an inert atmosphere after which the reaction medium containing the serotonine is recovered characterised in that the solvent for the coffee wax is a compound having the general formula II:

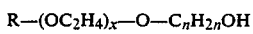    II wherein R is hydrogen or an alkyl group containing 1 to 4 carbon atoms, x is 0 or 1 and n is an integer from 2 to 4 with the proviso that x cannot have a value of 1 when n is 3 or 4.

The following classes of solvents are comprised within the general formula II:

(a) ethylene glycol and its ether derivatives
(b) propylene glycols and their ether derivatives
(c) diethylene glycol and its ether derivatives Preferred solvents are ethylene glycol monobutyl ether and diethylene glycol monomethyl ether.

Preferably, the solvent has a boiling point of at least 120° C. and a melting point no higher than 30° C. The solvent should not substantially react with the new compounds obtained nor substantially hinder the later stages of the process and, in addition should be substantially chemically stable under drastic conditions. The solvent enables the water and strong base to be introduced into the lipid phase.

The amount of solvent used may be, for instance, from 20% to 75% by weight and preferably from 30% to 50% by weight based on the weight of the coffee wax.

As stated in the above-mentioned French patents, serotonine is present in coffee wax in the form of amides. The alkaline hydrolysis breaks the amide bond and liberates the serotonine as well as the corresponding fatty acids. The strong base used for the hydrolysis may be, for example, sodium or potassium hydroxide. However, potassium hydroxide is preferred because it does not form solid soaps with the fatty acids which are liberated. The various parameters which govern the alkaline hydrolysis or saponification of the coffee wax are those conventionally used for saponification, e.g., the pH should be of the order of 12 to 14 and the amount of alkali used is advantageously from 10% to 50% by weight and preferably from 20% to 40% by weight based on the weight of coffee wax. In addition, since the alkaline hydrolysis takes place very slowly at lower temperatures, it is preferably carried out at temperatures from 120° C. to 160° C. and especially from 130° C. to 150° C. for a time advantageously from 3 to 6 hours. The reaction may also take place at temperatures from 160° C. to 180° C. for a time of from 1 to 3 hours. The hydrolysis is desirably carried out at atmospheric pressure using from 3 to 10% preferably from 4 to 7.5% of water based on the weight of coffee wax. Amounts of water greater than 10% may be used but cause an increase in pressure and while it is possible to use amounts above about 25% there is nothing beneficial in doing so. The alkaline hydrolysis must be effected in an inert atmosphere, for example, under nitrogen, because serotonine is very sensitive to oxygen in an alkaline medium. Preferably the reaction medium is agitated vigorously. The coffee wax that is generally available is a by-product from the decaffeination of green coffee and therefore is rich in caffeine. Although the process according to the invention may be effected using ordinary coffee wax, it is preferred to employ decaffeinated coffee wax, because caffeine is likely to be converted into caffeidine during the alkaline hydrolysis, which lowers the yield of serotonine.

The serotonine may be isolated from the reaction medium which contains it by conventional methods, exploiting the fact that serotonine is a compound which has basic characteristics and thus has a minimum solubility in water at pH about 10.8 (its isoelectric point).

The present invention also provides a process for the preparation of N-acetyl serotonine characterised in that serotonine is acetylated to form N, O-diacetyl serotonine which is then treated with an alkaline mixture of water and a lower alcohol to selectively hydrolyse the O-acetyl group of the N, O-diacetyl serotonine to give N-acetyl serotonine.

The serotonine used for the process may be obtained by any method, and may conveniently be prepared from coffee wax, preferably by the process of this invention. The acetylation may be carried out by conventional means, for instance, by the addition of excess acetylating agent, preferably acetic anhydride. The acetylation forms a mixture containing a major part of N, O-diacetyl serotonine together with a small amount of the desired N-acetyl serotonine. These two acetylated derivatives are advantageously extracted from the acetylation medium by means of a solvent substantially insoluble in water, e.g., iso-butanol, preferably at pH 7, and then conveniently concentrating the organic phase to obtain an oil containing the two acetylated derivatives. This oil is then selectively hydrolysed, conveniently by dissolving in an alkaline mixture of water and alcohol in an amount from 2.5 to 7.5 times the volume of oil, preferably at a pH above 11 to produce the N-acetyl serotonine. The alcohol preferably has a boiling point below 100° C. and conveniently contains from 1 to 4 carbon atoms and is conveniently methanol, ethanol, n-propanol or isopropanol. The selective hydrolysis may conveniently be carried out at a temperature from 15° C. to 50° C., preferably from 25° C. to 40° C., over a suitable period of time, for instance from 15 to 60 minutes. The pH may be adjusted by the addition of 30% sodium hydroxide solution.

The present invention further provides a process for the preparation of melatonine characterised in that N-acetyl serotonine is methylated in the 5-position. Any conventional methylating agent may be used, especially dimethyl sulphate, which may, for instance, be added in excess to the aqueous-alcoholic solution of N-acetyl serotonine prepared as hereinbefore described. The pH is preferably above 11 and may be adjusted by adding a 30% sodium hydroxide solution while the temperature preferably does not exceed 45° C. During the reaction a considerable part of the melatonine crystallises and may be separated mechanically, e.g, by filtration after which the reaction medium may be extracted, by conventional means, with a suitable solvent to recuperate the remainder of the melatonine. Examples of solvents that may be used are dichloromethane, chloroform, isobutanol and higher alcohols, ethyl acetate and some fluoro-chloro alkanes e.g. Freons, Halons.

The present invention also provides a process for the production of mexamine characterised in that melatonine is deacetylated in a hot alkaline solution containing a substantially water-insoluble alcohol and then washed with water after which the alcohol phase is separated from the aqueous phase and acidified with hydrochloric acid.

Conveniently, the reaction mixture is cooled, for instance to ambient temperature, before washing with water.

The hot alkaline solution preferably contains sodium hydroxide and the temperature is conveniently above 90° C., and desirably at reflux. The alcohol preferably contains from 4 to 8 carbon atoms and may be, for example, isobutanol, a pentanol, a hexanol or a benzyl alcohol. After washing with water the alcohol phase is preferably acidified to a pH of less than 3 and then, if desired, concentrated. The mexamine crystallises and may be separated by conventional means. The mexamine is advantageously prepared from melatonine produced as hereinbefore described in accordance with the present invention.

The following Examples further illustrate the present invention.

EXAMPLES

Example 1

Extraction of serotonine 700 g of decaffeinated coffee wax containing 5% water were hydrolysed under an inert atmosphere of nitrogen after the addition of 300 g ethyleneglycol monobutyl ether, 200 g of potassium hydroxide and 12 g of sodium dithionite. After 4 hours reaction at 140° C., the amides of serotonine were completely hydrolysed, and the mixture was cooled to 75° C., diluted with 1000 g water and then acidified with 420 g of 32% hydrochloric acid. The aqueous phase which formed was separated and the organic phase again extracted with 1200 g of 0.1% hydrochloric acid at 75° C. After separation, the two aqueous phases were mixed, neutralised to pH 7 and filtered. 3000 g of a solution containing 32 g of serotonine were obtained.

Example 2

Preparation of N-acetyl serotonine

To the aqueous solution of serotonine obtained in Example 1, there were added 40 g acetic anhydride while maintaining the pH between 8-9 with 30% sodium hydroxide at 25° C. to 30° C. N, O-diacetyl serotonine formed, having the appearance of an insoluble gum, and was extracted twice with 500 g isobutanol. The extract thus obtained was concentrated to obtain 80 g of an oil which was dissolved in a mixture containing 320 parts water and 80 parts ethanol. The pH was adjusted to 12.5 with 30% sodium hydroxide and the solution maintained at about 30° C. for 30 minutes, which provokes the selective hydrolysis of the O-acetyl group. The solution then contained 36 g N-acetyl serotonine.

Example 3

Preparation of melatonine

To the aqueous alcoholic solution containing N-acetyl serotonine prepared in Example 2, there were added slowly and simultaneously 36 g of dimethyl sulphate and 20 g of 30% sodium hydroxide so that the pH was maintained at 12.5, while ensuring that the temperature did not exceed 40° C. During this operation, a part of the melatonine formed crystallised and this was filtered after neutralisation. The mother-liquor of crystallisation was decolourised with activated carbon, concentrated to eliminate the ethanol, then extracted with dichloromethane. After separation of the aqueous phase, the organic phase was concentrated to dryness which allowed the recuperation of a further 28 g of crude melatonine. The two fractions, which totalled 42 g, were mixed and purified by recrystallisation in a mixture containing water and ethanol in a 75:25 ratio. 30 g of white crystals of melatonine were obtained having a purity of 98.6%.

Example 4

Preparation of mexamine

The melatonine obtained in Example 3 was taken up in 300 g isobutanol To this mixture were added 30 g sodium hydroxide and 3 g of sodium dithionite and the whole mixture was refluxed at 105° C. for 2 hours under nitrogen. The reaction mixture was then cooled and extracted with 500 g water. The aqueous phase which contained sodium acetate formed as well as excess sodium hydroxide, was separated. The isobutanol phase was acidified to pH 2 with 32% hydrochloric acid and then concentrated which induced the crystallisation of the mexamine which was then filtered. 36 g of crude mexamine was thus obtained. After recrystallisation in 96% ethanol 30 g of white crystals of mexamine were obtained having a purity of 98.5%.

Example 5

A similar procedure to that described in Examples 1 to 4 was followed except that diethyleneglycol-monomethylether was used instead of ethyleneglycol monobutyl ether as the hydrolysis solvent in the extraction of serotonine from coffee wax. 98.5% pure crystals of mexamine were obtained.

We claim:

1. A process for the preparation of melatonine which comprises reacting N-acetyl serotonine in an aqueous-alcoholic-alkaline solution with an excess of dimethyl sulphate at a temperature no higher than 45° C. and separating melatonine from the solution.

2. A process according to claim 1 wherein the melatonine is separated from the aqueous-alcoholic-alkaline solution by filtration and by extracting the filtered solution with a solvent and recuperating melatonine from the solvent.

3. A process according to claim 1 wherein the pH of the aqueous-alcoholic-alkaline solution is above 11.

4. A process according to claim 1 wherein the aqueous-alcoholic-alkaline solution comprises an alcohol having from 1 to 4 carbon atoms.

5. A process according to claim 1 wherein the aqueous-alcoholic-alkaline solution comprises an alcohol selected from the group consisting of methanol, ethanol, n-propanol and isopropanol.

6. A process according to claim 1 wherein the temperature is no higher than 40° C.

7. A process for the preparation of melatonine which comprises reacting N-acetyl serotonine in an aqueous-alcoholic-alkaline solution including an alcohol having from 1 to 4 carbon atoms with an excess of a methylating agent at a temperature no higher than 45° C. and separating melatonine from the solution.

8. A process according to claim 7 wherein the melatonine is separated from the aqueous-alcoholic-alkaline solution by filtration and by extracting the filtered solution with a solvent and recuperating melatonine from the solvent.

9. A process according to claim 7 wherein the pH of the solution is above 11.

10. A process according to claim 7 wherein the alcohol is selected from the group consisting of methanol, ethanol, n-propanol and isopropanol.

11. A process according to claim 7 wherein the temperature is no higher than 40° C.

12. A process for the preparation of mexamine comprising reacting N-acetyl serotonine in an aqueous-alcoholic-alkaline solution with an excess of a methylating agent at a temperature no higher than 45° C. and separating melatonine from the solution and then mixing the melatonine with a substantially water-insoluble alcohol, heating the melatonine and alcohol mixture under alkaline conditions to form a reaction mixture, then washing the reaction mixture with water thereby forming an alcohol phase and an aqueous phase and then separating the alcohol phase from the aqueous phase and then acidifying the alcohol phase with hydrochloric acid and separating mexamine from the acidified alcohol phase.

13. A process for the preparation of mexamine which comprises mixing melatonine with a substantially water-insoluble alcohol, heating the melatonine and alcohol mixture under alkaline conditions to form a reaction mixture, then washing the reaction mixture with water thereby forming an alcohol phase and an aqueous phase and then separating the alcohol phase from the aqueous phase and then acidifying the alcohol phase with hydrochloric acid and then separating mexamine from the acidified alcoholic phase.

14. A process according to claim 13 wherein the mexamine is separated from the acidified alcoholic phase by filtering.

15. A process according to claim 13 further comprising recrystallyzing the mexamine.

16. A process according to claim 13 wherein the melatonine and alcohol mixture under alkaline conditions is heated at a temperature above 90° C.

17. A process according to claim 13 wherein the melatonine and alcohol mixture under alkaline conditions is heated at reflux temperature.

18. A process according to claim 13 wherein the alcohol phase is acidified to a pH of less than 3.

19. A process according to claim 13 wherein the alcohol contains from 4 to 8 carbon atoms.

20. A process according to claim 13 wherein the alcohol is selected from the group consisting of isobutanol, pentanols, hexanols and benzyl alcohols.

21. A process according to claim 13 wherein sodium hydroxide is added to the melatonine and alcohol mixture to effect the alkaline conditions.

* * * * *

UNITED STATES PATENT AND TRADEMARK OFFICE
CERTIFICATE OF CORRECTION

PATENT NO. : 4,772,726

DATED : September 20, 1988

INVENTOR(S) : Raymond BERTHOLET, et al.

It is certified that error appears in the above-identified patent and that said Letters Patent is hereby corrected as shown below:

Column 1, line 8, "July 1-83" should be --July 1, 1983--.

Column 3, line 62, "e.g," should be --e.g.,--.

Column 4, line 8, delete the period after "cooled" and insert a comma.

Column 5, line 17, after "isobutanol" insert a period.

Column 5, line 28, after "ethanol" insert a comma.

Signed and Sealed this

Twenty-eighth Day of February, 1989

Attest:

DONALD J. QUIGG

Attesting Officer

Commissioner of Patents and Trademarks